(12) United States Patent
Lee et al.

(10) Patent No.: US 8,764,946 B2
(45) Date of Patent: *Jul. 1, 2014

(54) DIVIDING WALL DISTILLATION COLUMNS FOR PRODUCTION OF HIGH-PURITY 2-ETHYLHEXANOL AND FRACTIONATION METHOD USING SAME

(75) Inventors: Sung Kyu Lee, Daegu (KR); Jong Ku Lee, Daejeon (KR); Joon Ho Shin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 315 days.

This patent is subject to a terminal disclaimer.

(21) Appl. No.: 13/256,430

(22) PCT Filed: Mar. 19, 2010

(86) PCT No.: PCT/KR2010/001725
§ 371 (c)(1),
(2), (4) Date: Sep. 13, 2011

(87) PCT Pub. No.: WO2010/107283
PCT Pub. Date: Sep. 23, 2010

(65) Prior Publication Data
US 2012/0004473 A1      Jan. 5, 2012

(30) Foreign Application Priority Data

Mar. 19, 2009  (KR) .................. 10-2009-0023464
Mar. 19, 2010  (KR) .................. 10-2010-0024649

(51) Int. Cl.
*B01D 3/14* (2006.01)
*C07C 31/125* (2006.01)

(52) U.S. Cl.
CPC .............. *B01D 3/141* (2013.01); *C07C 31/125* (2013.01)

USPC ............ 202/161; 202/158; 202/262; 568/913

(58) Field of Classification Search
CPC ............................... B01D 3/141; C07C 31/125
USPC ............................ 202/158, 161, 262; 568/913
See application file for complete search history.

(56) References Cited

U.S. PATENT DOCUMENTS 2,471,134 A * 5/1949 Wright .......................... 196/111
3,969,196 A   7/1976 Zosel
(Continued)

FOREIGN PATENT DOCUMENTS

DE         10330934       2/2005
EP         1181964        2/2002
(Continued)

*Primary Examiner* — Nina Bhat
*Assistant Examiner* — Jonathan Miller
(74) *Attorney, Agent, or Firm* — McKenna Long & Aldridge LLP (57) ABSTRACT

Disclosed is a dividing wall distillation column for producing high-purity 2-ethyl hexanol that includes a condenser, a reboiler and a main column having a dividing wall, where the main column is divided into a column-top zone, an upper feed zone, an upper outflow zone, a lower feed zone, a lower outflow zone and a column-bottom zone, a raw material flows in a middle inflow plate in which the upper feed zone and the lower feed zone come in contact with each other, a low boiling point component flows out from the column-top zone, a high boiling point component flows out from the column-bottom zone, and a middle boiling point component flows out through a middle outflow plate in which the upper outflow zone and the lower outflow zone come in contact with each other, and the middle boiling point component is 2-ethyl hexanol.

2 Claims, 7 Drawing Sheets

(56) References Cited

U.S. PATENT DOCUMENTS

| | | | |
|---|---|---|---|
| 6,117,277 A | 9/2000 | Zgorzelski et al. | |
| 6,649,028 B2 * | 11/2003 | Sakamoto et al. | 203/98 |
| 7,288,169 B2 * | 10/2007 | Yada et al. | 202/158 |
| 8,242,308 B2 * | 8/2012 | Ho et al. | 562/600 |
| 2003/0139631 A1 | 7/2003 | Muller et al. | |
| 2009/0253934 A1 * | 10/2009 | Ho et al. | 562/600 |
| 2010/0137630 A1 | 6/2010 | Garton et al. | |
| 2011/0172462 A1 * | 7/2011 | Ligon et al. | 562/600 |
| 2012/0226074 A1 * | 9/2012 | Ho et al. | 562/600 |

FOREIGN PATENT DOCUMENTS

| | | |
|---|---|---|
| EP | 1323698 | 7/2003 |
| JP | 49-11365 | 3/1974 |
| JP | 4911365 A | 3/1974 |
| JP | 09-299702 | 11/1997 |
| JP | 09299702 A | 11/1997 |
| JP | 11-500437 | 1/1999 |
| JP | 11500437 A | 1/1999 |
| JP | 11-315051 | 11/1999 |
| JP | 11315051 A | 11/1999 |
| JP | 2004-517136 | 6/2004 |
| JP | 2004517136 A | 6/2004 |
| JP | 2005-298488 | 10/2005 |
| JP | 2005298488 A | 10/2005 |
| KR | 10-0410705 B1 | 3/2004 |
| KR | 10-2003-0057363 | 7/2006 |
| KR | 10-2007-0025556 | 3/2007 |
| KR | 10-0804821 | 2/2008 |
| WO | WO 9626173 | 8/1996 |
| WO | 2008116542 A | 10/2008 |
| WO | WO 2008/116542 | 10/2008 |

* cited by examiner

Figure 1

PRIOR ART

FIG. 2

PRIOR ART

FIG. 3

PRIOR ART

FIG. 4

PRIOR ART

DIVIDING WALL DISTILLATION COLUMNS FOR PRODUCTION OF HIGH-PURITY 2-ETHYLHEXANOL AND FRACTIONATION METHOD USING SAME

This application is a National Stage Entry of International Application No. PCT/KR2010/001725, filed Mar. 19, 2010, and claims priority to and the benefit of Korean Patent Application Nos. 10-2009-0023464, filed on Mar. 19, 2009 and 10-2010-0024649, filed on Mar. 19, 2010, which are hereby incorporated by reference in their entirety for all purposes as if fully set forth herein.

TECHNICAL FIELD

The present invention relates to a dividing wall distillation column for producing high-purity 2-ethyl hexanol, and a fractional distillation method using the same.

BACKGROUND ART

In general, various source materials such as crude oil are often present as a mixture of numerous chemicals. Therefore, the source materials themselves are hardly used in industries, but are generally separated into respective compounds that are used in industries. A distillation process is representative of chemical processes for separating a mixture.

In general, the distillation process serves to separate the mixture into two components: a high boiling point component and a low boiling point component. Therefore, the distillation columns whose number (n−1) is smaller than the number (n) of components in the mixture to be separated by 1 are used. That is to say, a process of separating a three-component mixture has mainly used a structure in which two distillation columns are continuously operated on site in conventional distillation industries.

Figure 1:
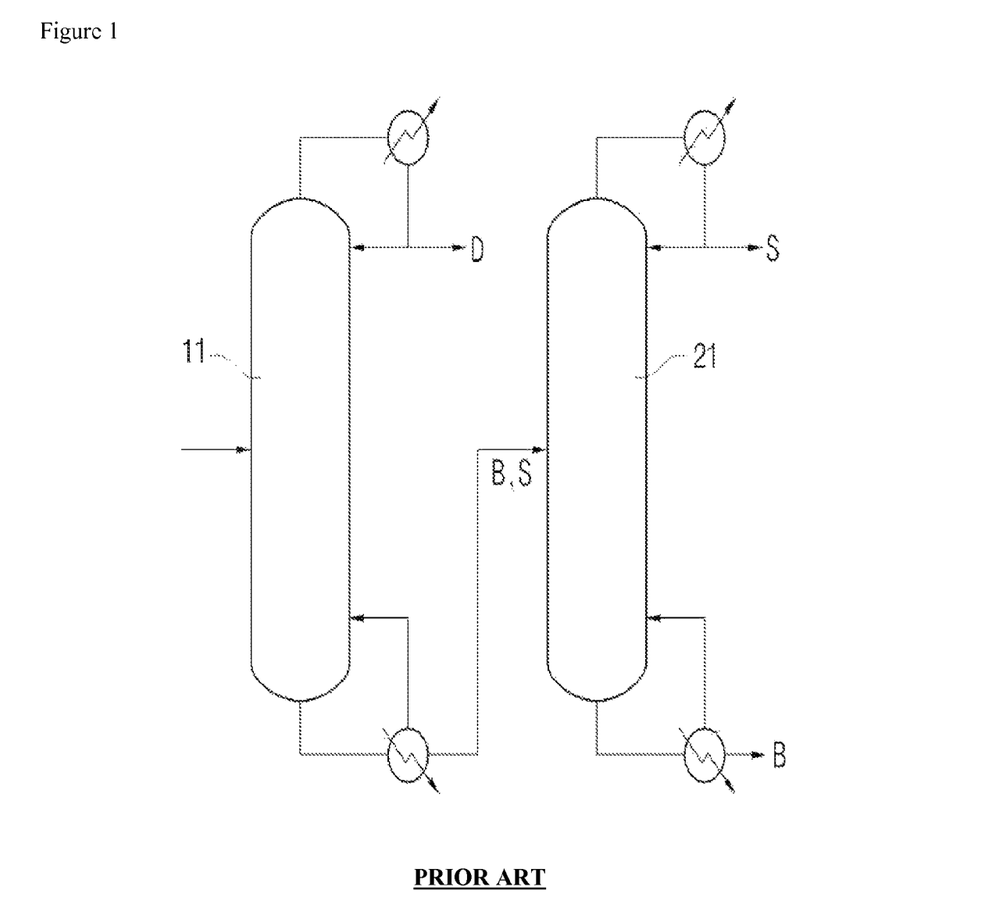
FIG. 1 is a schematic view showing a conventional distillation process of separating a three-component mixture.

A conventional distillation process of separating a three-component mixture is shown in FIG. 1.

The conventional distillation process uses a two-column system in which a lowermost boiling point component (D) is separated in a first column 11, and a middle boiling point component (S) and a high boiling point component (B) are separated in a second column 21.

Figure 2:
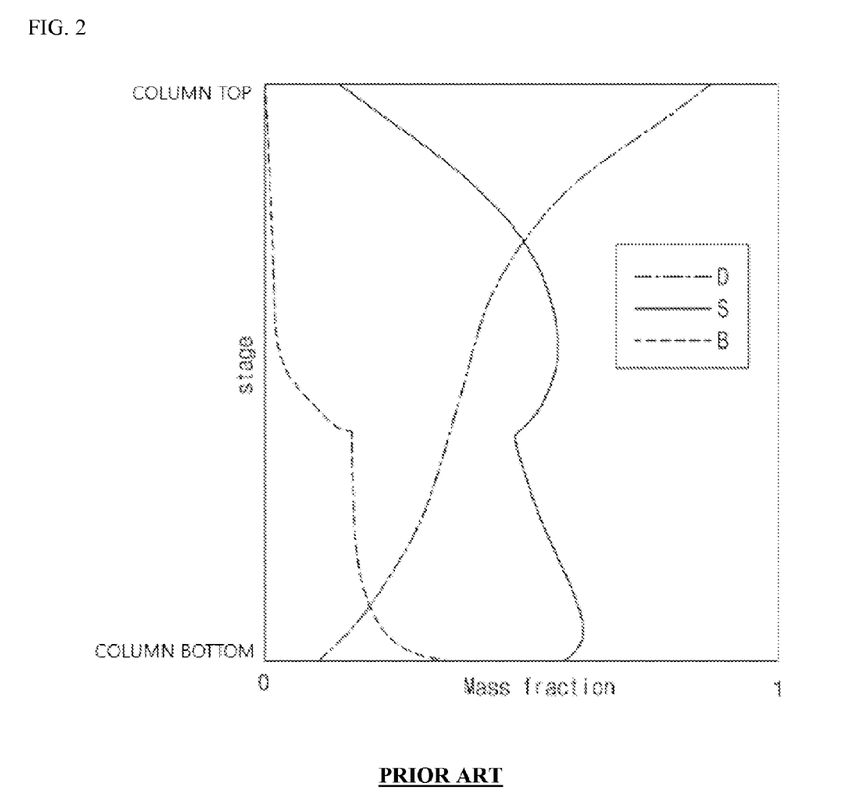
FIG. 2 shows a compositional profile in a first column in a conventional process of distilling alcohols.
Figure 3:
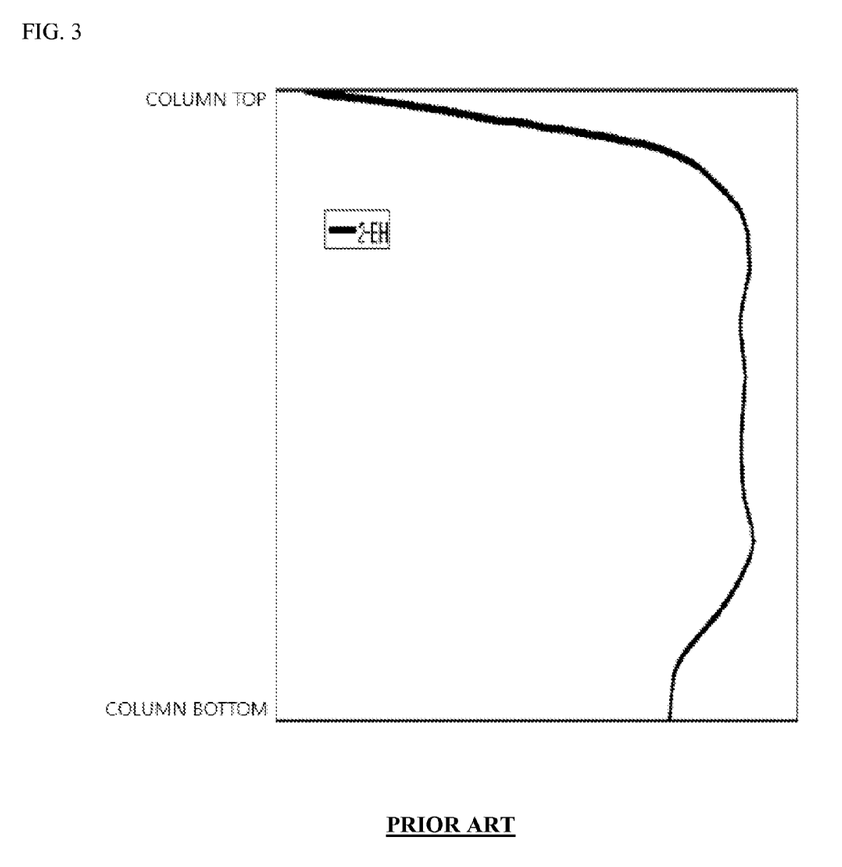
FIG. 3 shows a compositional profile in the first column when octanol (2-ethyl hexanol) is separated as a middle boiling point component.

In a conventional two-column distillation system which is a conventional process of distilling alcohols, a compositional profile in a first column is shown in FIG. 2. As shown in FIG. 2, the middle boiling point component (S) may be generally remixed in a lower section of the first column. In particular, a compositional profile in the first column when octanol such as 2-ethyl hexanol is separated as the middle boiling point component is shown in FIG. 3. As shown in FIG. 3, it can be seen that the octanol may be remixed in the lower section of the first column.

The above-described conventional distillation process can easily control a composition of a product, but the middle boiling point component is remixed in the first distillation column. Therefore, a thermodynamic efficiency in the distillation column is degraded, resulting in unnecessary consumption of energy.

Figure 4:
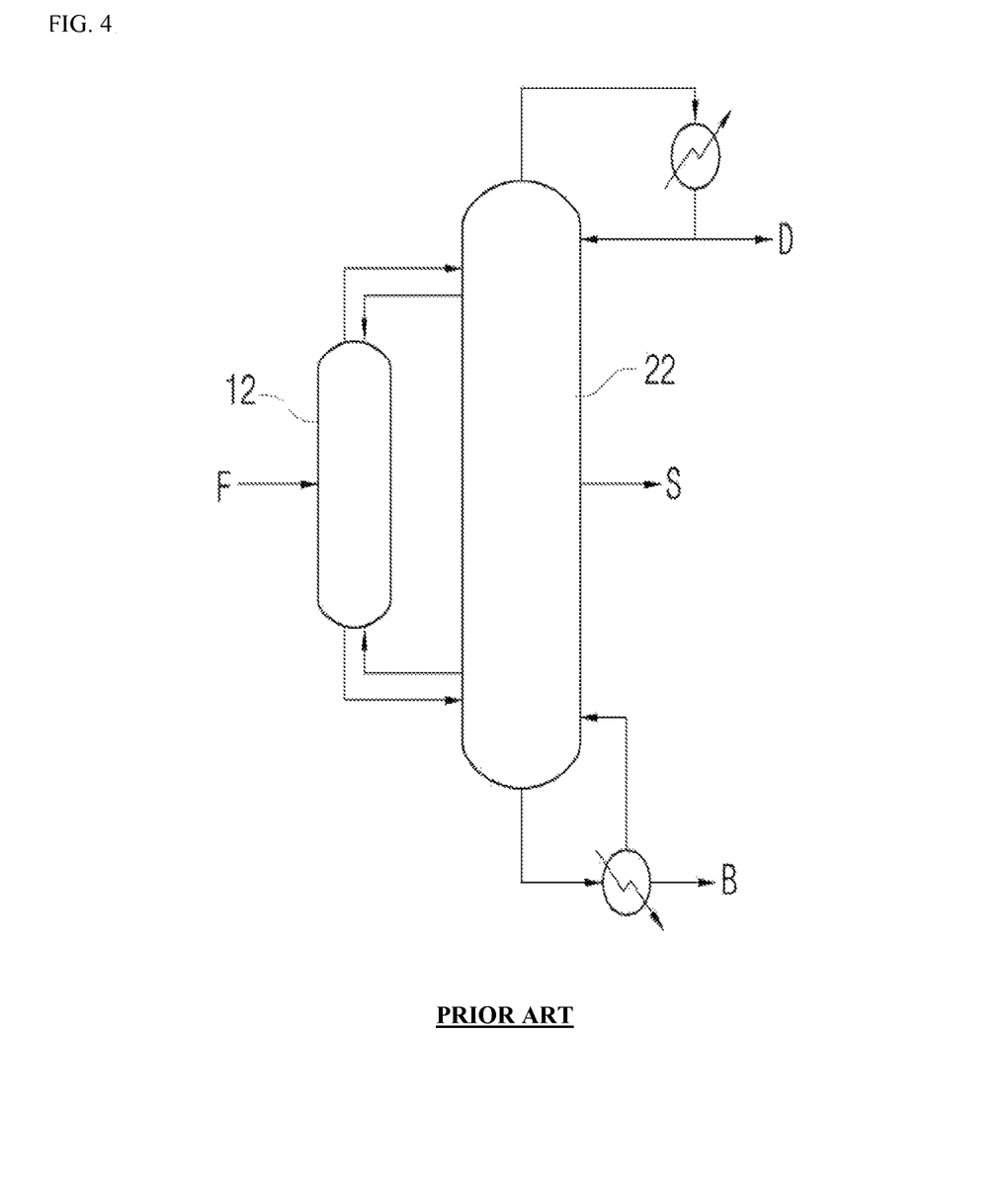
FIG. 4 is a schematic view showing a structure of a Petlyuk distillation column.

In order to solve these problems, much research on a new distillation structure has been conducted. A representative example of improving a separation efficiency using a thermally coupled structure may be a structure of a Petlyuk distillation column as shown in FIG. 4. The Petlyuk distillation column is arranged in a structure in which a preliminary separator 12 and a main separator 22 are thermally coupled. Therefore, a low boiling point component and a high boiling point component are primarily separated in the preliminary separator, and then flow to a feed plate of the main separator through a column-top portion and a column-bottom portion of the preliminary separator. Thereafter, the low boiling point, middle boiling point, and high boiling point components are separated in the main separator. This structure has high energy efficiency since a distillation curve in the Petlyuk distillation column is similar to an equilibrium distillation curve. However, the design and operation of a process are not easy, and the balance of pressure in the distillation column is particularly difficult to adjust.

In order to solve the problems regarding the Petlyuk distillation column, a dividing wall distillation column (DWC) has been proposed. A thermodynamic aspect of the DWC is similar to that of the Petlyuk distillation column, but a structural aspect is different from that of the Petlyuk distillation column in that a dividing wall is installed in a distillation column to integrate the preliminary separator of the Petlyuk distillation column in the main separator. Such a structure is highly advantageous in that operations are easily performed since the problems regarding the balance between the preliminary separator of the Petlyuk distillation column and the main separator are naturally solved and thus operations are simple, and the investment costs may also be significantly reduced since two types of distillation columns are integrated into one.

Korean Patent No. 080482 filed by and issued to this applicant discloses a conventional technique associated with the refinement of 2-ethyl hexanol.

The above-described technique relates to a purification method including passing a byproduct, which is generated in a plant for preparing 2-ethyl hexanol from butylaldehyde through an aldol condensation reaction and a hydrogenation reaction, through two multi-stage distillation columns to recover 2-ethyl hexanol and 2-ethylhexyl-2-ethyl hexanoate, characterized in that the byproduct includes 100 parts by weight of 2-ethyl hexanol, 2 to 6 parts by weight of a butylaldehyde trimer, 7 to 12 parts by weight of 2-ethylhexyl-2-ethyl hexanoate and 0.01 to 0.3 parts by weight of a high boiling point component, and the method includes passing the by-product through a first multi-stage distillation column to recover 2-ethyl hexanol and distilling a residual substance in a second multi-stage distillation column under the operating conditions such as an operating pressure of 980.665 to 9806.650 kPa and an operating temperature of 150 to 200° C. to recover 2-ethylhexyl-2-ethyl hexanoate.

Such a technique uses two columns like conventional processes, but the present invention is quite different from this technique in that it is not directed to a distillation column including a dividing wall.

DISCLOSURE

Technical Problem

In spite of the advantages of the above-mentioned dividing wall distillation column, the dividing wall distillation column is hardly installed on site the distillation industry. One important reason for this is that the dividing wall distillation column is inflexible in a variation in operating conditions due to the structural characteristics in which a flow rate of an internally circulating material cannot be controlled once the dividing wall distillation column is designed, unlike the Petlyuk distillation column. That is to say, an exact simulation and a structural determination are required at the beginning of the design of the distillation column.

In recent years, much research on the structure and control of the dividing wall distillation column has been conducted, but the details of the design structures and operating conditions of the dividing wall distillation column such as a position of a feed plate, setting of a dividing wall section, a position of a plate for producing a middle boiling point component, a total number of plates, a distillation temperature and a distillation pressure are very restrictive in the distillation column.

Particularly, since the design structures such as a plate number of the distillation column and a position of a feed plate, and the operating conditions such as distillation temperature and pressure should be changed according to the natures of a compound to be fractionally distilled, it is difficult to use the dividing wall distillation column.

Therefore, in order to solve the above-mentioned problems, reduce energy consumption and the costs of equipment, the present invention is directed to providing a dividing wall distillation column having a suitable design to purify 2-ethyl hexanol and a method of operating the same.

Technical Solution

Therefore, the present invention is designed to solve the above problems, and an object of the present invention is to provide a dividing wall distillation column including a condenser, a reboiler, and a main column having a dividing wall formed therein. Here, the main column is divided into a column-top zone, an upper feed zone, an upper outflow zone, a lower feed zone, a lower outflow zone and a column-bottom zone. Also, a crude 2-ethyl hexanol raw material (F) flows in a middle inflow plate NR1 in which the upper feed zone and the lower feed zone come in contact with each other, a low boiling point component (D) flows out from the column-top zone, a high boiling point component (B) flows out from the column-bottom zone, and a middle boiling point component (S) flows out through a middle outflow plate NR2 in which the upper outflow zone and the lower outflow zone come in contact with each other. In this case, the middle boiling point component is 2-ethyl hexanol.

Also, the raw material (F) may have a 2-ethyl hexanol content of 90% by weight or more.

In addition, the number of plates provided respectively in the column-top zone, the upper feed zone, the upper outflow zone, the lower feed zone, the lower outflow zone and the column-bottom zone may be in a range of 80 to 145% of a theoretical plate number, as calculated from a distillation curve.

Additionally, a length of the dividing wall may be determined according to the total theoretical plate number in the upper feed zone and the lower feed zone.

Also, a length of the dividing wall may be in a range of 30 to 85% of the total theoretical plate number in the column-top zone, the upper feed zone, the lower outflow zone and the column-bottom zone, as calculated from the distillation curve.

In addition, a temperature of the column-top zone may be in a range of 75 to 85° C. at a pressure of 16.671 kPa.

Additionally, a temperature of the column-bottom zone may be in a range of 145 to 160° C. at a pressure of 16.671 kPa.

Moreover, a temperature of the middle outflow plate NR2, which is provided in a position where the upper outflow zone and the lower outflow zone come in contact with each other, and from which the middle boiling point component (S) flows out, may be in a range of 130 to 140° C. at a pressure of 16.671 kPa.

Also, the temperature of the column-top zone may be in a range of a lower temperature limit ($T_{1\alpha}$) to an upper temperature limit ($T_{2\alpha}$), which follows the following Equation 1, when the pressure is out of a pressure of 16.671 kPa:

Lower limit: $T_{1\alpha} = 114.5099 * P^{0.2439}$

Upper limit: $T_{2\alpha} = 123.4949 * P^{0.2149}$      Equation 1

(wherein $T_{1\alpha}$ and $T_{2\alpha}$ represent temperatures (° C.); P represents a pressure (kPa), provided that $0.981 \leq P \leq 980.665$ and $P \neq 16.671$).

In addition, the temperature of the column-bottom zone may be in a range of a lower temperature limit ($T_{1\beta}$) to an upper temperature limit ($T_{2\beta}$), which follows the following Equation 2, when the pressure is out of a pressure of 16.671 kPa:

Lower limit: $T_{1\beta} = 192.1386 * P^{0.1548}$

Upper limit: $T_{2\beta} = 206.5980 * P^{0.1405}$      Equation 2

(wherein $T_{1\beta}$ and $T_{2\beta}$ represent temperatures (° C.); P represents a pressure (kPa), provided that $0.981 \leq P \leq 980.665$ and $P \neq 16.671$).

Additionally, the temperature of the middle outflow plate NR2, which is provided in a position where the upper outflow zone and the lower outflow zone come in contact with each other, and from which the middle boiling point component (S) flows out, may be in a range of a lower temperature limit ($T_{1\chi}$) to an upper temperature limit ($T_{2\chi}$), which follows the following Equation 3, when the pressure is out of a pressure of 16.671 kPa:

Lower limit: $T_{1\chi} = 157.7845 * P^{0.1034}$

Upper limit: $T_{2\chi} = 167.6350 * P^{0.096}$      Equation 3

(wherein $T_{1\chi}$ and $T_{2\chi}$ represent temperatures (° C.); P represents a pressure (kPa), provided that $0.981 \leq P \leq 980.665$ and $P \neq 16.671$).

Another aspect of the present invention provides a method of fractionally distilling 2-ethyl hexanol. Here, the method includes producing 2-ethyl hexanol using the above-described dividing wall distillation column.

Advantageous Effects

According to the present invention, since one distillation column can be used to realize the same effect as that obtained from the use of two distillation columns, the dividing wall distillation column can have an effect of reducing the costs of equipment to produce high-purity 2-ethyl hexanol, as well as an energy-reducing effect, compared to a conventional process system.

DESCRIPTION OF DRAWINGS

These and other features, aspects, and advantages of preferred embodiments of the present invention will be more fully described in the following detailed description, taken accompanying drawings. In the drawings.

BEST MODE

Hereinafter, preferred embodiments of the present invention will be described in detail with reference to the accompanying drawings.

The present invention provides a dividing wall distillation column including a condenser, a reboiler, and a main column having a dividing wall. Here, the main column is divided into a column-top zone, an upper feed zone, an upper outflow zone, a lower feed zone, a lower outflow zone and a column-bottom zone. Also, a crude 2-ethyl hexanol raw material (F) flows in a middle inflow plate NR1 in which the upper feed zone and the lower feed zone come in contact with each other, a low boiling point component (D) flows out from the column-top zone, a high boiling point component (B) flows out from the column-bottom zone, and a middle boiling point component (S) flows out through a middle outflow plate NR2 in which the upper outflow zone and the lower outflow zone come in contact with each other. In this case, the middle boiling point component is 2-ethyl hexanol.

Figure 5:
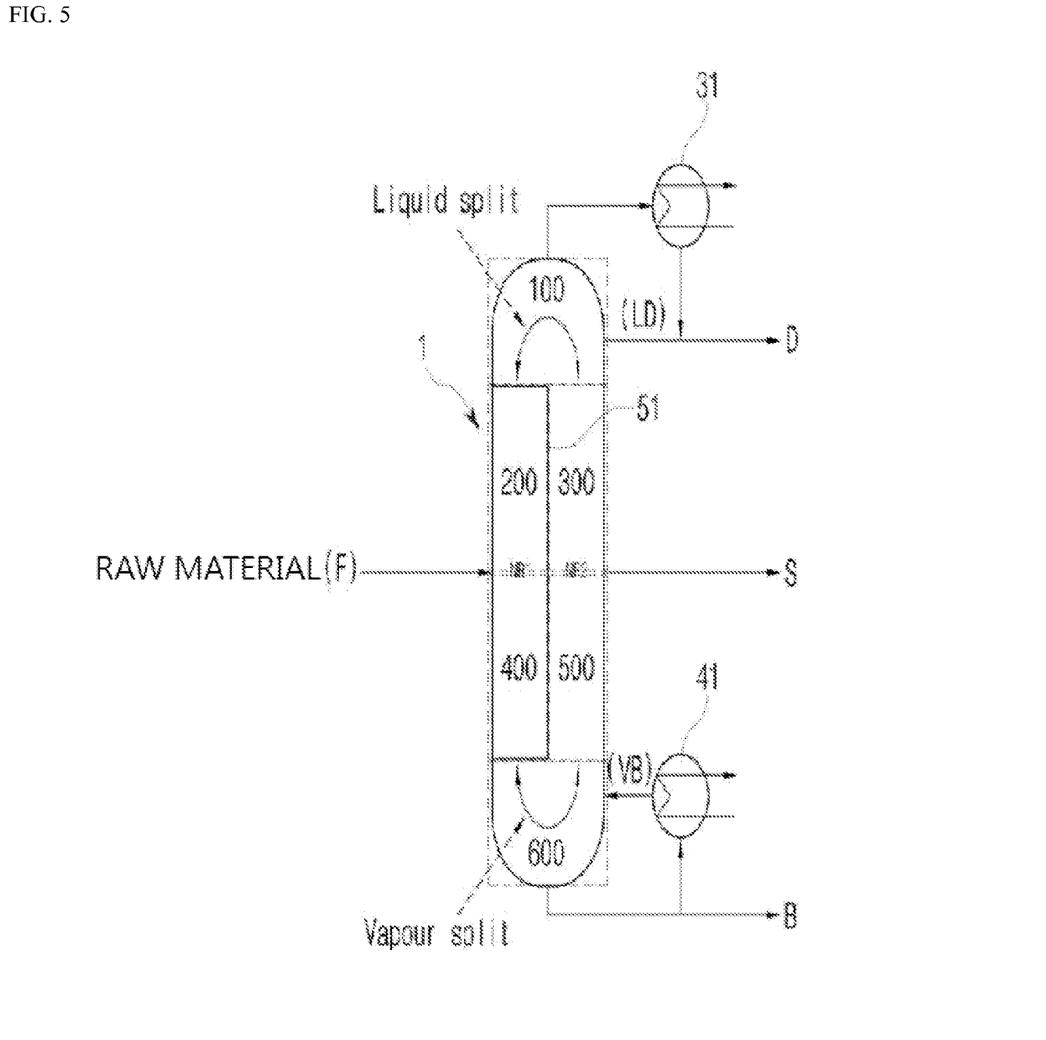
FIG. 5 is a schematic view showing a structure of a dividing wall distillation column according to the present invention.

A structure of the dividing wall distillation column according to the present invention is shown in FIG. 5.

The distillation column of the present invention includes a condenser 31 and a reboiler 41.

The condenser serves to condense a mixture in a gas state by depriving the mixture of evaporation heat. Here, a condenser used in a conventional chemical engineering system may be used without limitation.

The reboiler serves to vaporize a mixture in a liquid state by providing evaporation heat to the mixture. Here, a reboiler used in a conventional chemical engineering system may be used without limitation.

The main column 1 may be mainly divided into 6 sections.

The column-top zone 100 refers to an upper section of the main column that does not have a dividing wall installed therein.

The upper feed zone 200 is one of sections divided by the dividing wall, and is a sub-section arranged above a stream of an inflow material (raw material).

The upper outflow zone 300 is one of sections divided by the dividing wall, and is a sub-section arranged above a stream of an outflow material.

The lower feed zone 400 is the other one of the sections divided by the dividing wall, and is a sub-section arranged under a stream of the inflow material.

The lower outflow zone 500 is the other one of the sections divided by the dividing wall, and is a sub-section arranged under a stream of the outflow material.

The column-bottom zone 600 refers to a lower section of the main column that does not have a dividing wall installed therein.

The main column has at least one inflow point and at least three outflow points.

A raw material (F) such as crude 2-ethyl hexanol flows in a middle inflow plate NR1 in which the upper feed zone and the lower feed zone come in contact with each other, a low boiling point component (D) flows out from the column-top zone, a high boiling point component (B) flows out from the column-bottom zone, and a middle boiling point component (S) flows out through a middle outflow plate NR2 in which the upper outflow zone and the lower outflow zone come in contact with each other. In this case, the middle boiling point component (S) is 2-ethyl hexanol.

Here, the term "crude 2-ethyl hexanol raw material" refers to a target material (material to be distilled) used in the distillation process known in the art, which is a mixture including 2-ethyl hexanol as a main component, and the term "main component" refers to one component which is included in the largest amount among the respective components of the mixture. In order to obtain high-purity 2-ethyl hexanol, the crude 2-ethyl hexanol raw material preferably has a higher 2-ethyl hexanol content, and in order to obtain at least 99% by weight of the high-purity 2-ethyl hexanol, the crude 2-ethyl hexanol raw material preferably has a 2-ethyl hexanol content of at least 90% by weight.

According to the present invention, the expression "a middle boiling point component (S) is 2-ethyl hexanol," means that 2-ethyl hexanol is not 100% present but substantially present in the crude 2-ethyl hexanol raw material. The expression "2-ethyl hexanol is substantially present in the crude 2-ethyl hexanol raw material," means that a mixture itself is substantially considered 2-ethyl hexanol, particularly that the mixture includes 2-ethyl hexanol as a main component and has a higher 2-ethyl hexanol content than a fed raw material.

This dividing wall distillation process has lower energy consumption than a conventional distillation process using two continuous distillation columns, which may be derived from a structural difference. In the dividing wall distillation column, since spaces divided by the dividing wall serve as a preliminary separator, a composition of a liquid substantially corresponds to an equilibrium distillation curve due to separation of the high boiling point component and the low boiling point component, and a thermodynamic efficiency for separation is good due to suppression of a remixing effect.

The upper feed zone and the lower feed zone play a similar role as the preliminary separator which is operated in a conventional process (i.e., the upper feed zone and the lower feed zone may be generally referred to as a preliminary divisional section). A three-component mixture flowing in the preliminary divisional section is separated into a low boiling point component and a high boiling point component. Some of the low boiling point component and the high boiling point component separated in the preliminary divisional section flows in the column-top zone and the column-bottom zone, and some flows back in the upper outflow zone and the lower outflow zone and is re-distilled.

The upper outflow zone and the lower outflow zone serve as a main separator which is operated in a conventional process (i.e., the upper outflow zone and the lower outflow zone may be generally referred to as a main divisional section). Mainly, the low boiling point component and the middle boiling point component are separated in an upper portion of the dividing wall of the main divisional section, and the middle boiling point component and the high boiling point component are separated in a lower portion of the dividing wall.

The low boiling point component is passed through the column-top zone of the main column and the condenser, and some of the low boiling point component is then produced into a low boiling point product (D), and the rest flows back to the column-top zone of the main column at a liquid flux (LD). The high boiling point component is passed through the column-bottom zone of the main column and the reboiler, and some of the high boiling point component is then produced into a high boiling point product (B), and the rest flows back to the column-bottom zone of the main column at a vapor flux (VB).

The design of a thermally coupled distillation column system having a dividing wall is based on the design of a conventional thermally coupled distillation column, and the design of a distillation column having a minimum number of plates. The efficiency of the distillation column is maximal when a liquid compositional distribution of distillation plates in the distillation column is similar to an equilibrium distillation curve. Therefore, a minimum-plate distillation system is first designed on the assumption that a distillation column is operated under a pre-reflux handling. That is to say, the upper feed zone and the lower feed zone are designed on the assumption that a composition of a liquid is identical to that of a raw material in a raw material feed plate. Also, in the upper outflow zone and the lower outflow zone, a liquid composition is calculated from the middle to the column top of the distillation column using a cascade method for designing an equilibrium composition, starting from a concentration of the middle boiling point product. In the lower outflow zone serving as the main separator, a liquid composition is calculated from the middle to the column bottom of the distillation column using a cascade method of calculating an equilibrium composition, starting from a concentration of the middle boiling point product. Then, the plate number of the upper feed zone and the lower feed zone, which serve as the preliminary separator, and the plate number of the upper outflow zone and lower outflow zone, which serve as the main separator, may be determined from the distribution of the obtained liquid composition, respectively, by counting the number of raw material feed plates and the number of plates having a composition of a product. Here, since the obtained number of the plates in the distillation column is an ideal theoretical plate number, the plate number in the distillation column is preferably in a range of 80 to 145% of the theoretical plate number, depending on the conventional design standard. When the plate number is less than 80% of the calculated theoretical plate number, the low boiling point and high boiling point components are not easily separated in the preliminary divisional section, whereas when the plate number exceeds 145%, an energy-reducing effect is not increased as a section having a minimum reflux ratio, resulting in an increase in investment costs.

Also, a length of the dividing wall installed in the main column does not have a fixed value, and may be freely varied according to the kinds and components of a raw material to be processed. The length of the dividing wall is preferably determined according to the total theoretical plate number calculated based on the distillation curves of the upper feed zone and the lower feed zone.

In such a dividing wall distillation column, there are various method of calculating the theoretical plate number and amount of reflux by determining a spacing of the dividing wall using an equilibrium distillation curve method on a liquid composition with the preliminary divisional section and the main divisional section so as to design an optimal spacing of the dividing wall. However, the Fenske-Underwood equation is used to calculate the theoretical plate number according to the present invention (the Fenske-Underwood equation is widely known to those skilled in the art).

The length of the dividing wall is preferably in a range of 30 to 85% of the total theoretical plate number of the column-top zone, the upper feed zone, the lower outflow zone and the column-bottom zone, which are calculated based on the distillation curve. When the length of the dividing wall is less than 30%, some of the low boiling point component flows down from the preliminary divisional section, and may be introduced into a product in the main separator. On the other hand, when the length of the dividing wall exceeds 85%, it is difficult to maintain smooth equilibrium flow of liquid/vapor states of the low boiling point/middle boiling point components and liquid/vapor states of the middle boiling point/high boiling point components in the distillation column, which makes it difficult to manufacture a distillation column.

In the main column, a temperature of the column-top zone is preferably in a range of 75 to 85° C. at a pressure of 16.671 kPa. When the temperature of the column-top zone is less than 75° C., the low boiling point component (Light) may flow down from the preliminary divisional section, which affects the purity degree of a product. When the temperature of the column-top zone exceeds 85° C., the high boiling point component (Heavies) may flow up from the preliminary divisional section, which affects the purity degree of a product.

In the main column, a temperature of the column-bottom zone is preferably in a range of 145 to 160° C. at a pressure of 16.671 kPa. When the temperature of the column-bottom zone is less than 145° C., a middle boiling point component (2-ethyl hexanol) flows downwards as a product, which results in a decrease in production of the product. When the temperature of the column-bottom zone exceeds 160° C., a high boiling point component may laterally flow with the middle boiling point component.

A temperature of the middle outflow plate NR2, which is provided in a position where the upper outflow zone and the lower outflow zone come in contact with each other, and from which the middle boiling point component (S) flows out, is preferably in a range of 130 to 140° C. at a pressure of 16.671 kPa. When the temperature of the middle outflow plate NR2 is less than 130° C., it is difficult to remove a low boiling point component, whereas, when the temperature of the middle outflow plate NR2 exceeds 140° C., it is difficult to remove a high boiling point component, which affects the purity degree of a product.

In the main column, the temperature ranges of the column-top zone, the column-bottom zone and the middle outflow plate NR2 are based on a pressure of 16.671 kPa (i.e., a pressure somewhat reduced from a normal pressure). When the distillation column is operated at a reduced or compressed pressure, the temperature range may be varied. In general, the higher a pressure is, the higher an upper temperature limit and a lower temperature limit are.

In particular, when the column-top zone is out of a pressure of this pressure range, the temperature of the column-top zone may be in a range of an upper temperature limit ($T_{1\alpha}$) and a lower temperature limit ($T_{2\alpha}$), as calculated according to the following Equation 1:

Lower limit: $T_{1\alpha}=114.5099*P^{0.2439}$

Upper limit: $T_{2\alpha}=123.4949*P^{0.2149}$  Equation 1

(wherein $T_{1\alpha}$, and $T_{2\alpha}$ represent temperatures (° C.); P represents a pressure (kPa), provided that $0.981 \leq P \leq 980.665$ and $P \neq 16.671$).

Also, when the column-bottom zone is out of a pressure of this pressure range, the temperature of the column-bottom zone may be in a range of an upper temperature limit ($T_{1\beta}$) and a lower temperature limit ($T_{2\beta}$), as calculated according to the following Equation 2:

Lower limit: $T_{1\beta}=192.1386*P^{0.1548}$

Upper limit: $T_{2\beta}=206.5980*P^{0.1405}$  Equation 2

(wherein $T_{1\beta}$ and $T_{2\beta}$ represent temperatures (° C.); P represents a pressure (kPa), provided that $0.981 \leq P \leq 980.665$ and $P \neq 16.671$).

Additionally, when the middle outflow plate NR2 is out of a pressure of this pressure range, the temperature of the middle outflow plate NR2 may be in a range of an upper temperature limit ($T_{1\chi}$) and a lower temperature limit ($T_{2\chi}$), as calculated according to the following Equation 3:

Lower limit: $T_{1\chi} = 157.7845 * P^{0.1034}$

Upper limit: $T_{2\chi} = 167.6350 * P^{0.096}$    Equation 3

(wherein $T_{1\chi}$ and $T_{2\chi}$ represent temperatures (° C.); P represents a pressure (kPa), provided that $0.981 \leq P \leq 980.665$ and $P \neq 16.671$).

As described above, the operation conditions of the dividing wall distillation column according to the present invention, which reflect the temperatures of the column-top zone, the column-bottom zone and the middle outflow plate according to a variation in pressure, are listed as follows.

| | Lower limit | Upper limit |
|---|---|---|
| Pressure = 16.671 kPa | | |
| Temperature (° C.) of column-top zone | 75 | 85 |
| Temperature (° C.) of column-bottom zone | 145 | 160 |
| Temperature (° C.) of middle outflow plate | 130 | 140 |
| Pressure = 9.807 kPa | | |
| Temperature (° C.) of column-top zone | 65 | 75 |
| Temperature (° C.) of column-bottom zone | 135 | 150 |
| Temperature (° C.) of middle outflow plate | 125 | 135 |
| Pressure = 29.420 kPa | | |
| Temperature (° C.) of column-top zone | 85 | 95 |
| Temperature (° C.) of column-bottom zone | 160 | 175 |
| Temperature (° C.) of middle outflow plate | 140 | 150 |

As described above, the thermally coupled distillation column having a dividing wall according to the present invention is designed to improve the efficiency of the distillation column in a distillation system for distilling a mixture of three or more components. Therefore, the distillation column has the same effect as that obtained from the use of two distillation columns since a dividing wall is installed in the main column to form spaces, which have a liquid compositional distribution similar to the high-efficiency equilibrium distillation system and serve as the preliminary separator and the main separator.

Meanwhile, the present invention is directed to a method of fractionally distilling 2-ethyl hexanol. Here, the method includes producing 2-ethyl hexanol using the above-described dividing wall distillation column.

MODE FOR INVENTION

Hereinafter, the present invention will be described in further detail with reference to the following Examples. It should be understood that the descriptions proposed herein are merely preferable examples for the purpose of illustration only, and not intended to limit the scope of the invention.

Example 1

In order to verify the performances of the distillation systems proposed in the present invention, a dividing-wall distillation column (DWC) was designed and operated. It was confirmed that it is possible to obtain a composition of a product required through an actual operation of the system. Two conventional distillation columns having no dividing wall were used in Comparative Example 1, and one distillation column provided with a dividing wall was used in Example 1. A content of 2-ethyl hexanol in the raw material was set to 96.09% by weight in both of Comparative Example 1 and Example 1.

Figure 6:
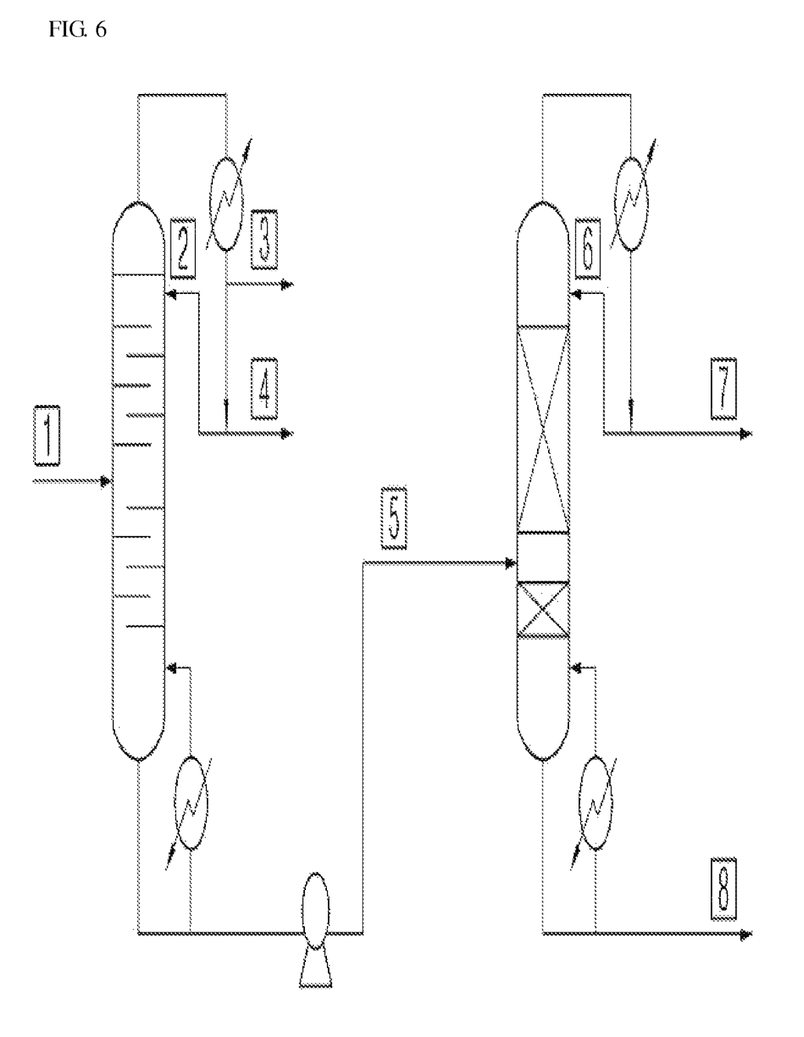
FIG. 6 is a schematic view showing dividing wall distillation column described in Comparative Example 1.
Figure 7:
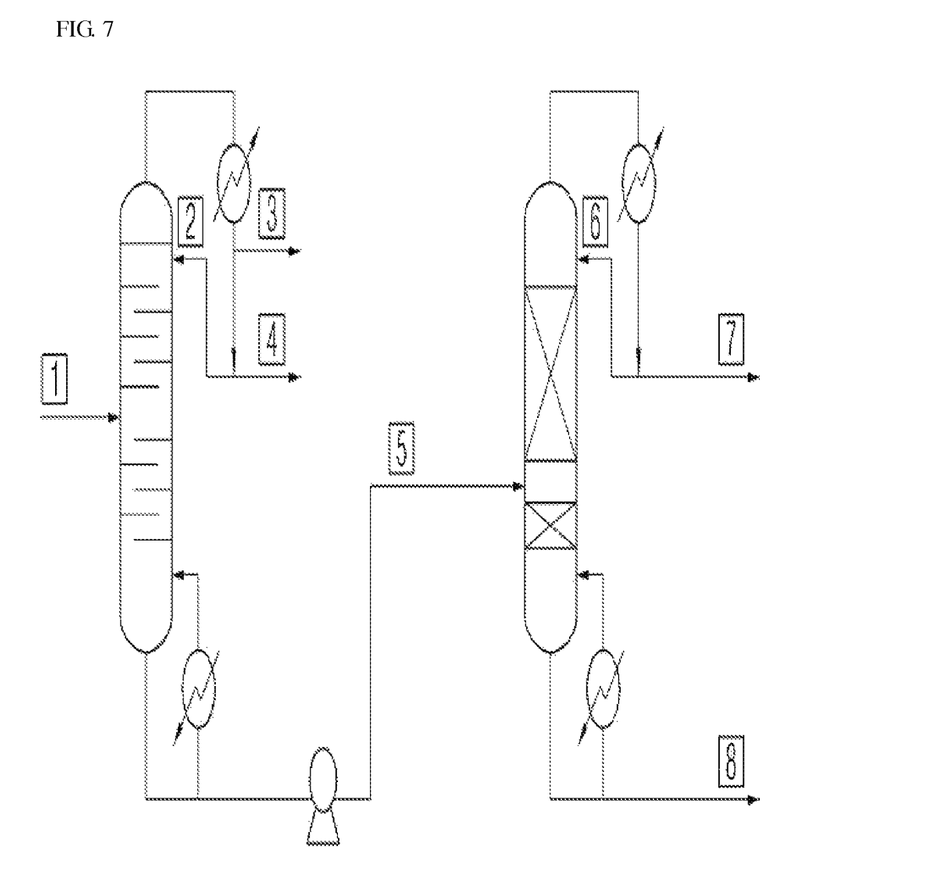
FIG. 7 is a schematic view showing dividing wall distillation column described in Example 1.

The distillation columns described in Comparative Example 1 and Example 1 are shown in FIGS. 6 and 7, respectively. Reference numerals 1 to 8 in FIGS. 6 and 7 represent respective streams as described in Example 1 and Comparative Example 1.

The distillation columns of Example 1 and Comparative Example 1 had theoretical plate numbers as listed in Table 1. In the distillation column of Example 1, a length of the dividing wall was set to the theoretical plate number of 54, which corresponded to 84% of the total theoretical plate number in the column-top zone, the upper feed zone, the lower outflow zone and the column-bottom zone.

The experimental results are listed in the following Tables 2 and 3.

TABLE 1

| | | Theoretical plate number |
|---|---|---|
| Example | Column-top zone 100 | 13 |
| | Upper feed zone 200 | 15 |
| | Upper outflow zone 300 | 37 |
| | Lower feed zone 400 | 6 |
| | Lower outflow zone 500 | 24 |
| | Column-bottom zone 600 | 12 |
| Comparative Example | First column | 33 |
| | Second column | 49 |

TABLE 2

| | | | Units | 1 | 2 | 3 | 4 | 5 | 6 | 7 | 8 |
|---|---|---|---|---|---|---|---|---|---|---|---|
| Comparative Example | Condition | Temperature | ° C. | 90.6 | 50.0 | 50.0 | 50.0 | 162.3 | 64.9 | 64.9 | 152.1 |
| | | Pressure | kPa | 490.333 | 16.671 | 16.671 | 16.671 | 490.333 | 24.517 | 24.517 | 49.033 |
| | | Flow rate | kg/hr | 11262.7 | 2761.0 | 131.0 | 310.0 | 10821.7 | 8509.3 | 10461.3 | 360.4 |
| | Composition | H$_2$O | wt % | 1.20 | 8.53 | 82.37 | 8.53 | 0.02 | 0.02 | 0.02 | 0.00 |
| | | Light | | 1.58 | 49.48 | 17.64 | 49.48 | 0.01 | 0.01 | 0.01 | 0.00 |
| | | 2-EH | | 96.09 | 32.72 | 0.00 | 32.72 | 99.11 | 99.76 | 99.76 | 80.39 |
| | | Heavies | | 1.13 | 9.27 | 0.00 | 9.27 | 0.86 | 0.21 | 0.21 | 19.61 |
| Example | Condition | Temperature | ° C. | 90.6 | 50.0 | 50.0 | 50.0 | 135.0 | 153.0 | — | — |
| | | Pressure | kPa | 490.333 | 16.671 | 16.671 | 16.671 | 24.517 | 39.227 | — | — |
| | | flow rate | kg/hr | 11262.7 | 7460.0 | 121.0 | 320.0 | 10461.3 | 360.4 | — | — |
| | Composition | H$_2$O | | 1.20 | 8.53 | 82.37 | 8.53 | 0.02 | 0.00 | — | — |
| | | Light | wt % | 1.58 | 49.48 | 17.64 | 49.48 | 0.01 | 0.00 | — | — |

TABLE 2-continued

|  | Units | 1 | 2 | 3 | 4 | 5 | 6 | 7 | 8 |
|---|---|---|---|---|---|---|---|---|---|
| 2-EH |  | 96.09 | 32.72 | 0.00 | 32.72 | 99.76 | 80.39 | — | — |
| Heavies |  | 1.13 | 9.27 | 0.00 | 9.27 | 0.21 | 19.61 | — | — |

* 2-EH: 2-ethyl hexanol

TABLE 3

|  | Comparative Example | | | Example | Reduction ($\times 10^7$ KJ/hr) | Reduction rate (%) |
|---|---|---|---|---|---|---|
|  | Total | First column | Second column | | | |
| Energy consumption ($\times 10^7$ KJ/hr) | 1.68 | 0.54 | 1.14 | 1.11 | 0.57 | 34.0 |

As described in Example 1, it was revealed that 99% by weight of the high-purity 2-ethyl hexanol was effectively recovered due to suppression of the remixing effect and an increase in separation efficiency. An additional recycling process of refining 2-ethyl hexanol is not required due to an increase in purity degree of the product, thereby improving the productivity. The inventive DWC (one column and two heat exchangers) was much less expensive than the conventional distillation columns (two columns and four heat exchangers) in an aspect of the investment costs.

A reduction rate of energy was highly decreased by approximately 34.0%, compared to the conventional distillation columns.

The present invention has been described in detail. However, it should be understood that the detailed description and specific examples, while indicating preferred embodiments of the invention, are given by way of illustration only, since various changes and modifications within the scope of the invention will become apparent to those skilled in the art from this detailed description.

The invention claimed is:

1. A dividing wall distillation column comprising a condenser, a reboiler and a main column having a dividing wall, wherein the main column is divided into a column-top zone, an upper feed zone, an upper outflow zone, a lower feed zone, a lower outflow zone and a column-bottom zone,
a raw material flows in a middle inflow plate in which the upper feed zone and the lower feed zone come in contact with each other, a low boiling point component flows out from the column-top zone, a high boiling point component flows out from the column-bottom zone, and a middle boiling point component flows out through a middle outflow plate in which the upper outflow zone and the lower outflow zone come in contact with each other, wherein the raw material has a 2-ethyl hexanol content of 90% by weight or more, and
the middle boiling point component is 2-ethyl hexanol,
wherein the number of plates provided respectively in the column-top zone, the upper feed zone, the upper outflow zone, the lower feed zone, the lower outflow zone and the column-bottom zone is in a range of 80 to 145% of a theoretical plate number, as calculated from a distillation curve,
wherein a length of the dividing wall is in a range of 30 to 85% of the total theoretical plate number in the column-top zone, the upper feed zone, the lower outflow zone and the column-bottom zone, as calculated from the distillation curve,
wherein
(i) when the pressure is at a pressure of 16.671 kPa:
a temperature of the column-top zone is in a range of 75 to 85° C., a temperature of the column-bottom zone is in a range of 145 to 160° C., and a temperature of the middle outflow plate is in a range of 130 to 140° C.,
(ii) when the pressure is out of a pressure of 16.671 kPa:
the temperature of the column-top zone is in a range of a lower temperature limit ($T_{1\alpha}$) to an upper temperature limit ($T_{2\alpha}$), which follows the following Equation 1,
the temperature of the column-bottom zone is in a range of a lower temperature limit ($T_{1\beta}$) to an upper temperature limit ($T_{2\beta}$), which follows the following Equation 2,
the temperature of the middle outflow plate is in a range of a lower temperature limit ($T_{1\chi}$) to an upper temperature limit ($T_{2\chi}$), which follows the following Equation 3, Lower limit: $T_{1\alpha} = 114.5099 * P^{0.2439}$ Upper limit: $T_{2\alpha} = 123.4949 * P^{0.2149}$      Equation 1

(wherein $T_{1\alpha}$ and $T_{2\alpha}$ represent temperatures (° C.); P represents a pressure (kPa), provided that $0.981 \leq P \leq 980.665$ and $P \neq 16.671$)

Lower limit: $T_{1\beta} = 192.1386 * P^{0.1548}$

Upper limit: $T_{2\beta} = 206.5980 * P^{0.1405}$      Equation 2

(wherein $T_{1\beta}$ and $T_{2\beta}$ represent temperatures (° C.); P represents a pressure (kPa), provided that $0.981 \leq P \leq 980.665$ and $P \neq 16.671$)

Lower limit: $T_{1\chi} = 157.7845 * P^{0.1034}$

Upper limit: $T_{2\chi} = 167.6350 * P^{0.096}$      Equation 3

(wherein $T_{1\chi}$ and $T_{2\chi}$ represent temperatures (° C.); P represents a pressure (kPa), provided that $0.981 \leq P \leq 980.665$ and $P \neq 16.671$).

2. A method of fractionally distilling 2-ethyl hexanol comprising:
providing the raw material to the dividing wall column defined in claim 1; producing 2-ethyl hexanol from the dividing wall distillation column.

* * * * *